United States Patent
Hourigan et al.

(10) Patent No.: US 9,832,994 B2
(45) Date of Patent: Dec. 5, 2017

(54) THYMOL AND TOTAROL ANTIBACTERIAL COMPOSITION

(75) Inventors: Regina Hourigan, Metuchen, NJ (US); Rehana Gafur, Clifton, NJ (US); Jairajh Mattai, Piscataway, NJ (US); James Masters, Ringoes, NJ (US); Laurence Du-Thumm, Princeton, NJ (US); Shira Pilch, Highland Park, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/362,898

(22) PCT Filed: Dec. 15, 2011

(86) PCT No.: PCT/US2011/065024
§ 371 (c)(1),
(2), (4) Date: Jun. 4, 2014

(87) PCT Pub. No.: WO2013/089721
PCT Pub. Date: Jun. 20, 2013

(65) Prior Publication Data
US 2014/0314689 A1    Oct. 23, 2014

(51) Int. Cl.
*A01N 31/08* (2006.01)
*A61K 31/05* (2006.01)
*A61K 8/34* (2006.01)
*A61Q 17/00* (2006.01)
*A61Q 11/00* (2006.01)

(52) U.S. Cl.
CPC ........... *A01N 31/08* (2013.01); *A61K 8/34* (2013.01); *A61K 8/347* (2013.01); *A61K 31/05* (2013.01); *A61Q 11/00* (2013.01); *A61Q 17/005* (2013.01)

(58) Field of Classification Search
None
See application file for complete search history.

(56) References Cited

U.S. PATENT DOCUMENTS

| 2007/0054967 A1 | 3/2007 | Schmaus et al. |
| 2008/0194518 A1 | 8/2008 | Mookerjee et al. |
| 2009/0312279 A1 | 12/2009 | Mookerjee et al. |

FOREIGN PATENT DOCUMENTS

| CN | 1249929 A | 4/2000 |
| JP | 2011-105635 A | 6/2011 |
| WO | WO 97/01348 | 1/1997 |
| WO | WO 00/69277 | 11/2000 |
| WO | WO2005073154 | 8/2005 |
| WO | WO2006134160 | 12/2006 |
| WO | WO2008085446 | 7/2008 |
| WO | WO2010002571 | 1/2010 |
| WO | WO2010010320 | 1/2010 |
| WO | WO2010046238 | 4/2010 |
| WO | WO2010146142 | 12/2010 |

OTHER PUBLICATIONS

International Search Report and the Written Opinion issued in International Application PCT/US2011/065024 dated Nov. 9, 2012. WO.

Biochimica et Biophysica Acta (BBA)—Biomembranes vol. 1511, Issue 2, Apr. 2, 2001, pp. 281-290: http://www.sciencedirect.com/science/article/pii/S000527360100284X.

Smith E., et al., "The Phenolic Diterpene Totarol Inhibits Multidrug Efflux Pump Activity in Staphylococcus aureus. Antimicrobial Agents and Chemotherapy," Dec. 2007, p. 4480-4483, vol. 51, No. 12.

Jaiswal R., et al., "Totarol Inhibits Baterial Cytokinesis by Perturbing the Assembly Dynamics of FtsZ. Biochemistry," 46 (14), 4211-4220, 2007.

"Totarol is a phenolic diterpene extracted from the heartwood of the totara tree by the use of an organic solvent or near critical fluid, commercially available preparations using CO2. The resultant extract shows good antibacterial activity but needs to be included with a fungicide to offer complete protection against microbial contamination." Source: http://www.personalcaremagazine.com/Story.aspx?story=4456.

"Totarol, an extract from totara wood, has been shown to inhibit to multi-drug efflux pump of Staphylococcus aureus and sub-inhibitory concentrations were found to reduce the MICs of selected antibiotics. These results hold the promise of the use of plant extracts that may allow reduced concentrations of synthetic preservatives by potentiating their activity by blocking the effect of efflux pumps." http://www.personalcaremagazine.com/Story.aspx?Story=4456.

K. Roden, "Natural Preservatives: myth or magic?" Personal Care Magazine, Nov. 2008. Internet at: http://www.personalcaremagazine.com/Story.aspx?story=4456 (6 pages).

*Primary Examiner* — Dennis J Parad

(57) ABSTRACT

An antibacterial composition comprising thymol and totarol. This combination provides synergistic effect against gram negative and gram positive bacteria.

6 Claims, No Drawings

THYMOL AND TOTAROL ANTIBACTERIAL COMPOSITION

CROSS-REFERENCE TO RELATED PATENT APPLICATIONS

The present application is a U.S. national stage entry under 35 U.S.C. §371 of Patent Cooperation Treaty Patent Application No. PCT/US2011/65024, filed Dec. 15, 2011, the entirety of which is incorporated herein by reference.

FIELD OF THE INVENTION

The present invention relates to antibacterial compositions.

BACKGROUND OF THE INVENTION

Control of bacteria in products and on surfaces where products are used is an ongoing challenge. For example, *E. coli* is a challenging bacterium to control. Compared to gram positive bacteria, *E. coli* is a gram negative bacterium having an additional outer membrane and higher amounts of peptidoglycan in the cell wall. This is what makes *E. coli* more challenging to control. While some materials are known to provide some antibacterial effect, it is desired to develop improvements in these materials. One such improvement would be to provide bacterial kill while using less material.

BRIEF SUMMARY OF THE INVENTION

An antibacterial composition comprising thymol and totarol. This combination is synergistic for these two materials such that a lesser amount of either can be used.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

An antibacterial composition comprising thymol and totarol. The combination of thymol with totarol provides synergistic effect, which requires less of either material as compared to each material alone. The synergistic effect is effective against gram negative bacteria, such as *E. coli*, and gram positive bacteria, such as *S. aureus*.

Synergism is found when the fractional inhibitory concentration, which is calculated below, is found to be less than or equal to 0.75.

In certain embodiments, the weight ratio of thymol to totarol is 5:1 to 1:5. In other embodiments, the weight ratio is 3.21:1 to 1:3.21 or 1.56:1 to 1:1.56. In other embodiments, the weight ratio of thymol to totarol is one of 5:1, 1:5, 3.21:1, 1:3.21, 1.56:1, 1:1.56, or 1:1.

In the 1.56:1 to 1:1.56 range, the combination of thymol and totarol is synergistic for both the gram negative bacteria *E. coli* and the gram positive bacteria *S. aureus*.

In certain embodiments, the amount of thymol in the composition is 0.0001 to 2% by weight of the composition. In other embodiments, the amount is 0.0001 up to 1, 0.9, 0.8, 0.7, 0.6, 0.5, 0.4, 0.3, 0.2, or 0.1% by weight of the composition. In other embodiments, the amount is 0.0001 up to 0.5, 1, 1.5, or 2% by weight. In other embodiments, the amount is 0.0001 to 1% or 0.0001 to 0.5% by weight of the composition. In another embodiment, the amount is 0.5% by weight.

In certain embodiments, the amount of totarol in the composition is 0.0001 to 2% by weight of the composition. In other embodiments, the amount is 0.0001 up to 1, 0.9, 0.8, 0.7, 0.6, 0.5, 0.4, 0.3, 0.2, or 0.1% by weight of the composition. In other embodiments, the amount is 0.0001 up to 0.5, 1, 1.5, or 2% by weight. In other embodiments, the amount is 0.0001 to 1% or 0.0001 to 0.5% by weight of the composition. In another embodiment, the amount is 0.5% by weight.

This antibacterial combination of thymol and totarol is useful in personal care, oral care, and home care compositions. Examples of personal care compositions include, but are not limited to, body wash/shower gel, liquid hand cleanser, bar soap, shampoo, conditioner, antiperspirant/deodorants, and cosmetics. Examples of oral care compositions include, but are not limited to, dentifrices, toothpastes, tooth powders, prophylaxis pastes, mouth rinses, lozenges, gums, gels, paints, confectionaries, and denture cleaners. Examples of home care compositions include, but are not limited to, dish liquids, dish pastes, hard surface cleaners, fabric conditioners, and laundry detergents.

In certain embodiments, the thymol and totarol can be present in a body wash/shower gel, liquid hand cleanser, or shampoo in which each of these compositions include a surfactant. The thymol and totarol can also be included in a soap (fatty acid soap), which can be in the shape of a bar soap.

EXAMPLES

Minimum Inhibition Concentration (MIC)

Serial dilutions of the active are combined with tryptic soy broth and 0.1 optical density of bacteria in a 96 well plate. The optical density of the mixture is measured after 16-24 hours at 37° C. An increase in optical density represents bacterial growth. The plate is analyzed to determine the minimum concentration needed to inhibit growth of bacteria. Numbers are reported in ppm. The MIC values are determined for thymol and totarol against *E. Coli* and *S. aureus*. The MIC dose response assay is conducted just as the MIC, however, one active's concentration is kept constant and the other active's concentration follows a two-fold serial dilution.

Fractional Inhibition Concentration (FIC)

The MIC values are also determined for thymol in the presence of totarol to determine the Fractional Inhibitory Concentration (FIC). This calculation accounts for the fractional activity of thymol and totarol within a MIC test.

$$FIC = \frac{MIC \text{ of } (A) \text{ in mixture}}{MIC \text{ of } A \text{ alone}} + \frac{Mic \text{ of } (B) \text{ in mixture}}{MIC \text{ of } B \text{ alone}}$$

such that:

| FIC Value | Equivalant |
|---|---|
| x ≤ 0.75 | Synergism |
| 0.75 < x ≤ 1.3 | Additive |
| x ≥ 1.3 | Antagonistic |

TABLE 1

MIC and FIC Values for Thymol and Totarol

| Actives | E. coli | S. aureus |
|---|---|---|
| Thymol | 125 ppm | 125 ppm |
| Totarol | 125 ppm | 31.25 ppm |
| Mixture (fixed ratio of thymol:totarol 5:1) | 62.5 ppm thymol + 12.5 ppm totarol | 62.5 ppm thymol + 12.5 ppm totarol |
| FIC Value | 0.6 | 0.9 |
| Thymol | 125 ppm | 125 ppm |
| Totarol | 125 ppm | 31.25 ppm |
| Mixture (ratio of totarol:thymol 5:1) | 62.5 ppm totarol + 12.5 ppm thymol | 31.25 ppm totarol + 6.25 ppm thymol |
| FIC Value | 0.6 | 1.05 |
| Thymol | 125 ppm | 31.25 ppm |
| Totarol | 125 ppm | 31.25 ppm |
| Mixture (ratio of thymol:totarol 1.56:1) | 7.8 ppm thymol + 5 ppm totarol | 7.8 ppm thymol + 5 ppm totarol |
| FIC Value | 0.10 | 0.41 |
| Thymol | 125 ppm | 31.25 ppm |
| Totarol | 125 ppm | 31.25 ppm |
| Mixture (ratio of totarol:thymol: 1.56:1) | 7.8 ppm totarol + 5 ppm thymol | 7.8 ppm totarol + 5 ppm thymol |
| FIC Value | 0.10 | 0.41 |
| Thymol | 125 ppm | 31.25 ppm |
| Totarol | 125 ppm | 31.25 ppm |
| Mixture (ratio of totarol:thymol 3.21:1) | 7.8 ppm thymol + 25 ppm totarol | 7.8 ppm thymol + 25 ppm totarol |
| FIC Value | 0.26 | 1.04 |
| Thymol | 125 ppm | 31.25 ppm |
| Totarol | 125 ppm | 31.25 ppm |
| Mixture (ratio of thymol:totarol: 3.21:1) | 7.8 ppm totarol + 25 ppm thymol | 7.8 ppm totarol + 25 ppm thymol |
| FIC Value | 0.26 | 1.04 |

As can be seen from the table, the combination of thymol to totarol is synergistic for the gram negative bacteria *E. coli* in a 5:1 ratio to a 1:5 ratio. Also, when varying the ratio of thymol to totarol closer to 1:1, there is a broad spectrum synergistic activity against both the gram negative and the gram positive bacteria.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A method of controlling gram negative bacteria comprising contacting the gram negative bacteria with a composition comprising thymol and totarol, wherein a weight ratio of thymol to totarol is 5:1 to 1:5, and a Fractional Inhibition Concentration (FIC) Value of thymol and totarol is 0.6 or less.

2. The method of claim 1, wherein the gram negative bacteria is *E. coli*.

3. The method of claim 1, wherein the weight ratio of thymol to totarol is 3.21:1 to 1:3.21, and the Fractional Inhibition Concentration (FIC) Value of thymol and totarol is 0.26 or less.

4. The method of claim 1, wherein the weight ratio of thymol to totarol is 1.56:1 to 1:1.56, and the Fractional Inhibition Concentration (FIC) Value of thymol and totarol is 0.10 or less.

5. A method of controlling gram positive bacteria comprising contacting the gram negative bacteria with a composition comprising thymol and totarol, wherein a weight ratio of thymol to totarol is 1.56:1 to 1:1.56, and a Fractional Inhibition Concentration (FIC) Value of thymol and totarol is 0.41 or less.

6. The method of claim 5, wherein the gram positive bacteria is *S. aureus*.

\* \* \* \* \*